(12) United States Patent
Takahashi

(10) Patent No.: US 8,462,202 B2
(45) Date of Patent: Jun. 11, 2013

(54) IMAGING APPARATUS OF ELECTRONIC ENDOSCOPE AND ELECTRONIC ENDOSCOPE

(75) Inventor: Kazuaki Takahashi, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 1245 days.

(21) Appl. No.: 12/042,838

(22) Filed: Mar. 5, 2008

(65) Prior Publication Data

US 2008/0239071 A1 Oct. 2, 2008

(30) Foreign Application Priority Data

Mar. 29, 2007 (JP) ................. P2007-087026

(51) Int. Cl.
*H04N 13/00* (2006.01)
*A61B 1/04* (2006.01)

(52) U.S. Cl.
USPC ............................................. 348/76; 348/45

(58) Field of Classification Search
USPC ....................... 348/76, 45; 600/149
See application file for complete search history.

(56) References Cited

U.S. PATENT DOCUMENTS

| | | | | |
|---|---|---|---|---|
| 4,659,611 A | * | 4/1987 | Iwase et al. ................... | 428/209 |
| 4,805,598 A | * | 2/1989 | Ueda ............................. | 600/169 |
| 4,993,405 A | * | 2/1991 | Takamura et al. ........... | 600/110 |
| 5,604,018 A | * | 2/1997 | Horiuchi et al. .............. | 428/210 |
| 5,683,791 A | * | 11/1997 | Horiuchi et al. .............. | 428/210 |
| 5,691,794 A | * | 11/1997 | Hoshi et al. ................... | 349/158 |
| 5,702,807 A | * | 12/1997 | Horiuchi et al. .............. | 428/210 |
| 5,931,580 A | * | 8/1999 | Wyland ......................... | 374/141 |
| 6,040,612 A | * | 3/2000 | Minami et al. ................ | 257/432 |
| 6,557,721 B2 | * | 5/2003 | Yang ............................. | 220/713 |
| 6,716,161 B2 | * | 4/2004 | Higuma et al. ............... | 600/133 |
| 7,422,356 B2 | * | 9/2008 | Hama et al. ................... | 362/574 |
| 2003/0169575 A1 | * | 9/2003 | Ikuta et al. .................... | 361/761 |
| 2003/0180030 A1 | * | 9/2003 | Hirose et al. ................. | 385/147 |
| 2004/0188816 A1 | | 9/2004 | Minami et al. | |
| 2006/0152907 A1 | * | 7/2006 | Rathmann .................... | 361/720 |

FOREIGN PATENT DOCUMENTS

| | | |
|---|---|---|
| JP | 63-226334 A | 9/1988 |
| JP | 1-222579 A | 9/1989 |
| JP | 3-118021 A | 5/1991 |
| JP | 2000-147391 A | 5/2000 |
| JP | 2001-144447 A | 5/2001 |
| JP | 2003-173728 A | 6/2003 |
| JP | 2003-284686 A | 10/2003 |

OTHER PUBLICATIONS

Japanese Office Action for Japanese Application No. 2007-087026, issued on Oct. 3, 2012.

* cited by examiner

*Primary Examiner* — Patrice Winder
*Assistant Examiner* — Ebrahim Golabbakhsh
(74) *Attorney, Agent, or Firm* — Birch, Stewart, Kolasch & Birch, LLP

(57) ABSTRACT

An imaging apparatus is provided and includes: a solid-state imaging device that receives image light of an observed portion inside of a coelom to output an imaging signal of the image light; a cover glass disposed above an light receiving surface of the solid-state imaging device so that the cover glass and the solid-state imaging device are separated with a space; and a first circuit board disposed at a vicinity of an upper surface of the cover glass and including a peripheral circuit of the solid-state imaging device, the first circuit board having a thermal conductivity lower than that of a reference circuit board whose major component is alumina, the imaging apparatus being included in a front end of an electronic endoscope.

4 Claims, 4 Drawing Sheets

IMAGING APPARATUS OF ELECTRONIC ENDOSCOPE AND ELECTRONIC ENDOSCOPE

BACKGROUND OF THE INVENTION

1. Field of the Invention

The present invention relates to an imaging apparatus of an electronic endoscope for taking an image inside of the coelom, and an electronic endoscope including the imaging apparatus.

2. Description of Related Art

A medical diagnosis utilizing an electronic endoscope has been actively carried out in a medical field. A front end of an inserting portion of an electronic endoscope inserted into a coelom includes an imaging apparatus having a solid-state imaging device such as CCD and the like. An image inside of the coelom can be observed with a monitor by subjecting an imaging signal output from CCD to various signal processings by a processor apparatus.

The imaging apparatus includes the CCD mentioned above and an object optical system for taking in image light of an observed portion inside of the coelom, the image light being incident from an observation window provided at the front end of the inserting portion. A cover glass is arranged above an imaging surface (light receiving surface) of CCD to be spaced apart from each other therebetween by a gap (air gap).

Meanwhile, the front end of the inserting portion of the electronic endoscope inserted into the coelom is brought into a temperature to a degree the same as that of the physical temperature (about 37° C.). In contrast, a temperature inside of the inserting portion becomes higher than the physical temperature to be occasionally equal to or higher than 40° C. by heat of driving an electronic part of CCD or the like. In addition, there is a case of injecting cleaning water or air to the front end of the inserting portion when the observation window is stained, and therefore, a temperature difference is produced between a surface and the inner portion of the front end of the inserting portion. Therefore, when moisture is included inside of the inserting portion, there is a case in which dew condensation is produced on an object optical system or cover glass.

Particularly, an inner surface of the cover glass is proximate to an imaging surface of CCD, and therefore, a temperature thereof is liable to be high, on the other hand, there is a case in which an outer surface of the cover glass is rapidly cooled by injecting cleaning water or the like, and therefore, dew condensation is produced at an inner surface of the cover glass by moisture included in the air gap.

Further, in using an electronic endoscope which has been stored, when the electronic endoscope is connected to a processor apparatus and a power source is made ON, whereas a temperature of a solid-state imaging device rapidly rises immediately thereafter, a temperature of a member such as an object optical system and a cover glass gradually rises by receiving heat of the solid-state imaging device or a peripheral circuit. Therefore, immediately after making the power source ON, a temperature difference between the solid-state imaging device and the cover glass is large and dew condensation is liable to be produced.

Although when dew condensation is produced at the object optical system, a blurred image is simply brought about and an influence is not effected so much on observation, when dew condensation is produced on the inner surface of the cover glass as described above, the image quality is deteriorated considerably to a degree of being able to optically recognize water drops on an image and the observation becomes difficult. In view of such a background, various proposals have been made in order to prevent dew condensation of the inner surface of the cover glass (refer to JP-A-2003-284686).

JP-A-2003-284686 discloses an imaging apparatus of an electronic endoscope, in which a heat generating member such as a peripheral circuit of a solid-state imaging device is disposed at a vicinity of a cover glass to warm up an outer surface of the cover glass. JP-A-2003-284686 describes a first embodiment using only the peripheral circuit as a heat generating member, in addition, a second embodiment using a board extended substantially in a channel-like shape to surround the cover glass in three directions, and a third embodiment providing a heater in place of the peripheral circuit.

According to the invention described in JP-A-2003-284686, the peripheral circuit is mounted to the board. The board generally includes a material whose major component is alumina from reason of being inexpensive, easy to fabricate or the like. Generally, a heat conductivity of the board including the material whose major component is alumina is high, and therefore, heat of the peripheral circuit is escaped to a side of an operating portion on the hand side of the electronic endoscope by way of a wiring connected to the peripheral circuit. Therefore, even when a surface of the cover glass is intended to warm up by heat of the peripheral circuit, heat is not transferred efficiently to the surface of the cover glass. Therefore, according to the invention described in JP-A-2003-284686, it is necessary to use the extended board having a special shape or provide the heater, and hence fabrication cost and part cost are increased.

SUMMARY OF THE INVENTION

An object of an illustrative, non-limiting embodiment of the invention is to provide an imaging apparatus of an electronic endoscope and an electronic endoscope, which are capable of efficiently and firmly preventing dew condensation of a cover glass attached to a solid-state imaging device by an inexpensive constitution.

According to an aspect of the invention, there is provided an imaging apparatus of an electronic endoscope including: a solid-state imaging device that receives image light of an observed portion inside of a coelom to output an imaging signal of the image light; a cover glass disposed above an light receiving surface (imaging surface) of the solid-state imaging device so that the cover glass and the solid-state imaging device are separated with a space; and a first circuit board disposed at a vicinity of an upper surface of the cover glass and including a peripheral circuit of the solid-state imaging device, the first circuit board having a thermal conductivity lower than that of a circuit board whose major component is alumina, the imaging apparatus being included in a front end of an electronic endoscope.

The thermal conductivity of the first circuit board may be at least equal to or lower than 1/5 of the thermal conductivity of the circuit board whose major component is alumina.

The first circuit board may include a material whose major component is a mixture material of alumina and glass baked at a low temperature preferably less than 1,000° C., more preferably about 900° C.). In this case, the alumina may be mixed in an amount of 40 to 60%, and the glass may be mixed in an amount of 40 to 60% (incidentally, the total amount of the alumina and the glass does not exceed 100%).

The imaging apparatus may include a second circuit board disposed at a lower surface or a side surface of the solid-state imaging device and including a peripheral circuit of the solid-state imaging device, in which a thermal conductivity of the second circuit board is higher than that of the circuit board whose major component is alumina.

The thermal conductivity of the second circuit board may be at least 5 times as much as that of the circuit board whose major component is alumina.

The second circuit board may include a material whose major component is aluminum nitride baked at a high temperature (preferably more than 1,000° C., more preferably about 1,500° C.).

According to an aspect of the invention, there is provided an electronic endoscope including the imaging apparatus.

BRIEF DESCRIPTION OF THE DRAWINGS

The features of the invention will appear more fully upon consideration of the exemplary embodiment of the invention, which are schematically set forth in the drawings, in which.

DETAILED DESCRIPTION OF THE EXEMPLARY EMBODIMENTS

Although the invention will be described below with reference to exemplary embodiments thereof, the following exemplary embodiments and modifications do not restrict the invention.

In an imaging apparatus for an electronic endoscope and an electronic endoscope according to an exemplary embodiment of the invention, the cover glass is warmed up by the board having the thermal conductivity lower than the thermal conductivity of the circuit board whose major component is alumina, and therefore, dew condensation of the cover glass attached to the solid-state imaging device can efficiently and firmly be prevented by an inexpensive constitution.

Figure 1:
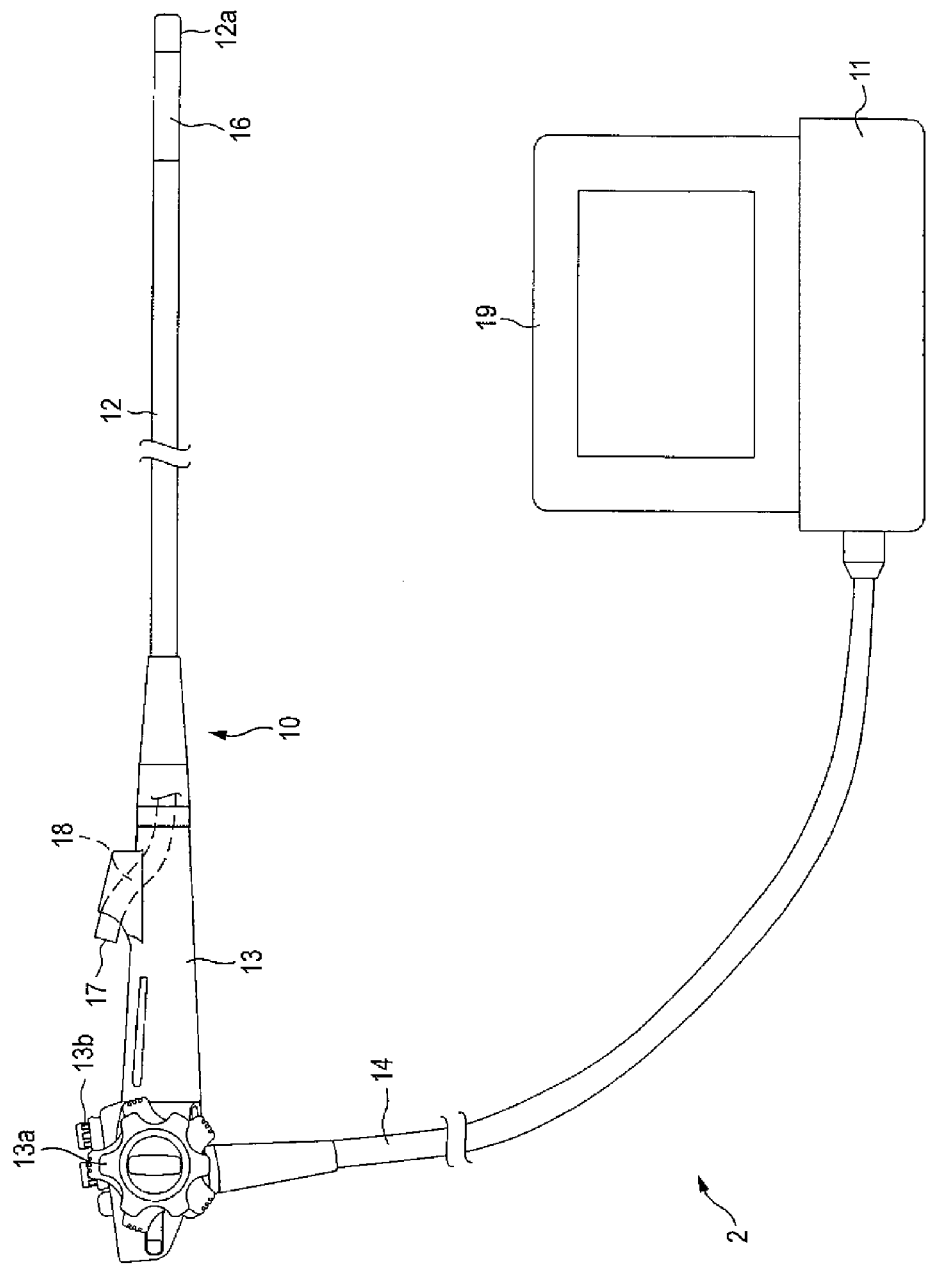
FIG. 1 is an outline view showing a constitution of an electronic endoscope system.

In FIG. 1, an electronic endoscope system 2 includes an electronic endoscope 10, a processor apparatus 11, and a light source apparatus (not illustrated) or the like. The electronic endoscope 10 includes an inserting portion 12 inserted into a coelom, an operating portion 13 continuously provided to a base end portion of the inserting portion 12, and a cord 14 connected to the processor apparatus 11 and the light source apparatus.

A front end portion 12a continuously provided to a front end of the inserting portion 12 includes an imaging apparatus 15 (refer to FIG. 2) for taking an image inside of the coelom. Further, a rear side of the front end portion 12a is provided with a bend portion 16 connected with a plurality of bend nodes. The bend portion 16 is operated to bend in an up and down direction and in a left and right direction by pushing and pulling a wire inserted into the inserting portion 12 by operating an angle knob 13a provided at the operating portion 13. Thereby, the front end portion 12a is directed in a desired direction inside of the coelom.

The operating portion 13 is provided with a forceps port 17 into which a treatment piece is inserted. The forceps port 17 is connected to a forceps channel 18 arranged inside of the inserting portion 12 as shown by a dotted line.

The processor apparatus 11 is provided with circuits (mentioned later) for subjecting an imaging signal acquired by the imaging apparatus 15 to various processings. The light source apparatus is mounted with a light source or the like for supplying illuminating light to the electronic endoscope 10 by way of the cord 14. An image inside of the coelom taken by imaging apparatus 15 is displayed on a monitor 19 connected to the processor apparatus 11.

Figure 2:
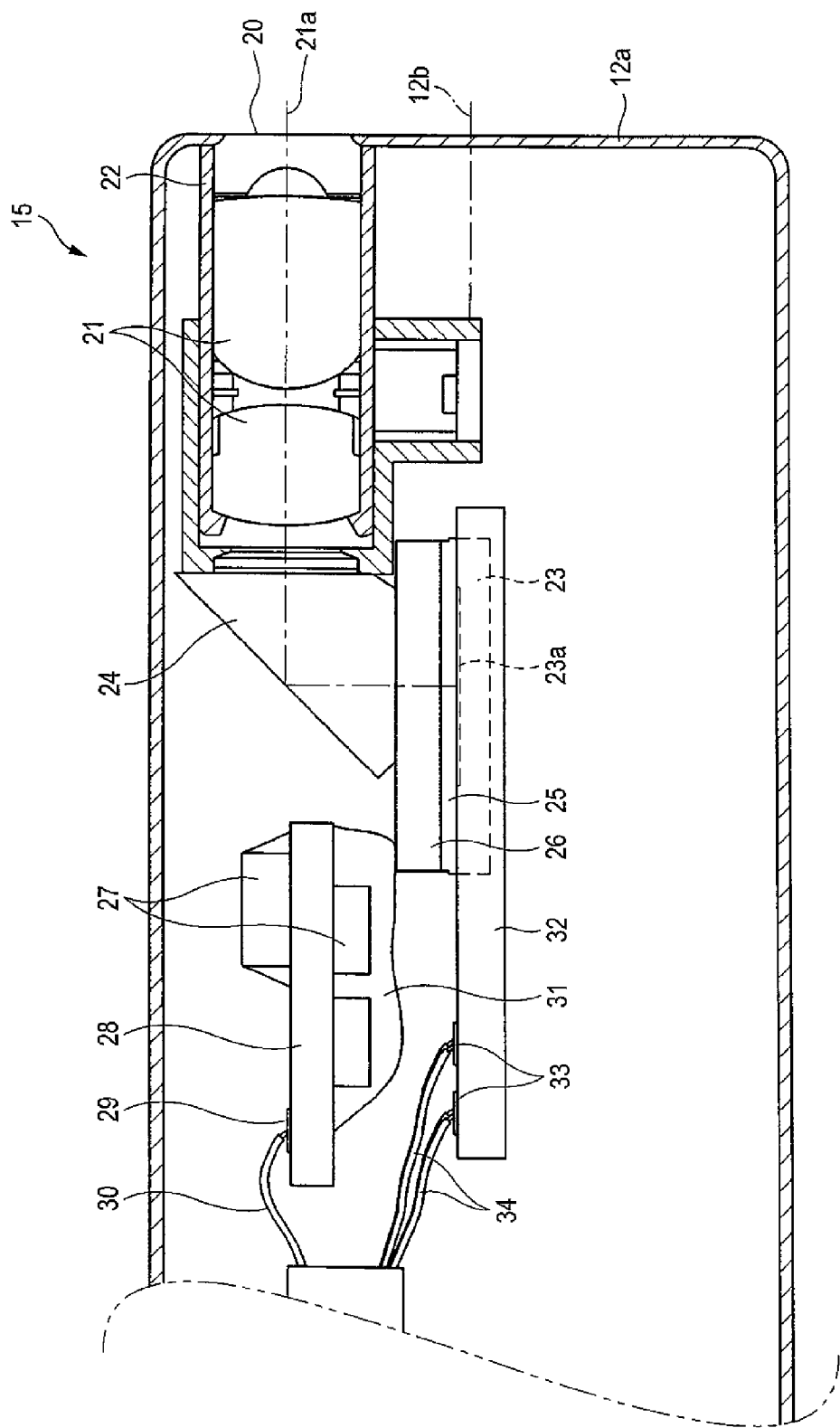
FIG. 2 is a sectional view of an enlarged portion showing a constitution of a front end of an inserting portion of an electronic endoscope.

In FIG. 2 showing a constitution of the imaging apparatus 15, the front end portion 12a is provided with an observation window 20. Inside of the observation window 20 is arranged a lens barrel 22 for holding an object optical system (lens group) 21 for taking in image light of the observed portion inside of the coelom. The lens barrel 22 is attached such that an optical axis 21a of the object optical system 21 becomes in parallel with a center axis 12b of the inserting portion 12. Further, although not illustrated, other than the observation window 20, the front end portion 12a is provided with an illumination window for illuminating illumination light from the light source apparatus at the observed portion inside of the coelom, a forceps outlet continuously provided to the forceps port 17 by way of the forceps channel 18, a nozzle for injecting cleaning water or air for removing stain of the observation window 20 by operating an air blowing/water delivering button 13b (refer to FIG. 1) and the like.

A rear end of the lens barrel 22 is connected with a prism 24 for guiding image light of the observed portion by way of the object optical system 21 to an imaging surface (light receiving surface) 23a of CCD 23. According to the prism 24, an incident surface thereof is connected to the object optical system 21, and an emitting surface thereof is connected to cover glass 26 mentioned later, respectively. Thereby, the optical axis 21a of the object optical system 21 and the imaging surface 23a are arranged to be parallel.

Figure 3:
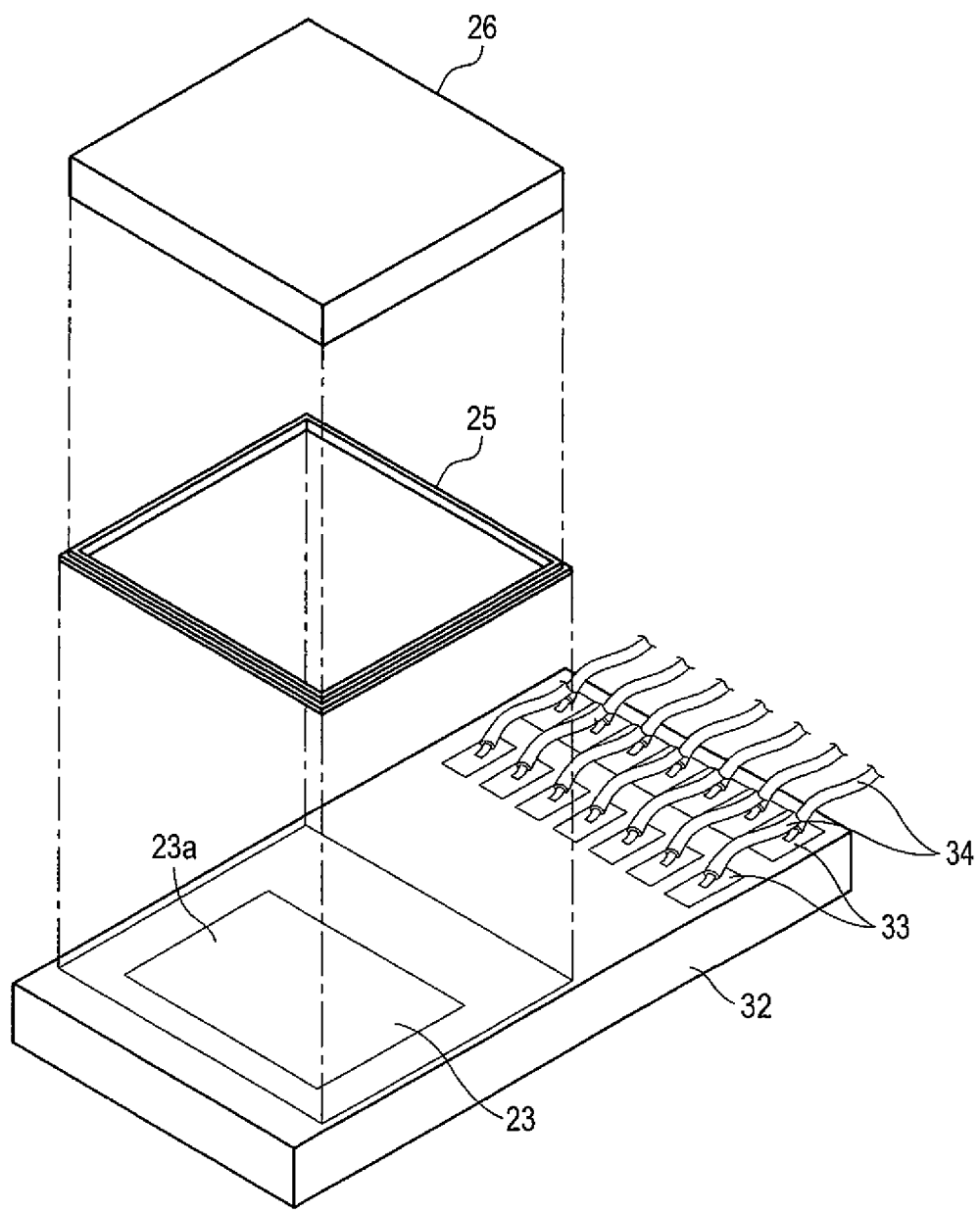
FIG. 3 is a disassembled perspective view showing constitutions of CCD, a spacer, a cover glass, and a second circuit board.

CCD 23 includes, for example, an interline type CCD, and a bare chip provided with the imaging surface 23a on a surface of the bare chip is used. Also as shown in FIG. 3, the cover glass 26 in a shape of a rectangular plate is attached onto the imaging surface 23a by way of a spacer 25 in a shape of a quadrangular frame. CCD 23, the spacer 25, and the cover glass 26 are integrated by being adhered to each other by an adhering agent.

A vicinity of an upper surface of the cover glass 26 is arranged with a first circuit board 28 mounted with a peripheral circuit 27. The peripheral circuit 27 is connected with a cable 30 by way of a terminal 29. The peripheral circuit 27 includes, for example, a circuit lowering an output impedance so as not to bring about signal attenuation or unnecessary reflection and achieving impedance matching. The peripheral circuit 27 is sealed by a sealing agent 31 of one-component curable epoxy resin or the like. The sealing agent 31 is brought into contact with a rear end of the cover glass 26, thereby, the first circuit board 28 is held at an illustrated position.

There is used the first circuit board 28 having a thermal conductivity lower than a thermal conductivity of a circuit board whose major component is alumina (alumina 90% or more, thermal conductivity 10 to 30 W/mK, for example, alumina 96%, thermal conductivity 14 to 18 W/mK). Specifically, the first circuit board 28 is provided with a thermal conductivity equal to or smaller than at least ⅕ of the thermal conductivity of the circuit board whose major component is alumina, or ⅕ through ¼ or less as a preferable range. As a material satisfying the above-described condition, for example, there is pointed out an alumina glass board (thermal conductivity 2 to 3 W/mK) mixed with alumina in an amount of 40 to 60%, and glass in an amount of 40 to 60% (incidentally, the total amount of the alumina and the glass does not exceed 100%) and formed by being baked at a high temperature. As amounts of the alumina and the glass, although it may be preferred that the amount of the alumina is 50% and the amount of the glass, a similar effect can be achieved even when other component in an amount of several percents is mixed thereto.

A lower surface of CCD 23 is provided with a second circuit board 32. The second circuit board 32 holds CCD 23 to cover a lower surface and a side surface of CCD 23. The second circuit board 32 is mounted with, for example, a circuit of transmitting a drive signal (not illustrated) for driving CCD 23 or the like as a peripheral circuit. A rear end portion of the second circuit board 32 extended to a rear end of the inserting portion 12 is provided with a plurality of input/output terminals 33. The input/output terminals 33 are soldered with signal lines 34 for intermediating in exchanging various signals with the processor apparatus 11 by way of the cord 14.

Figure 4:
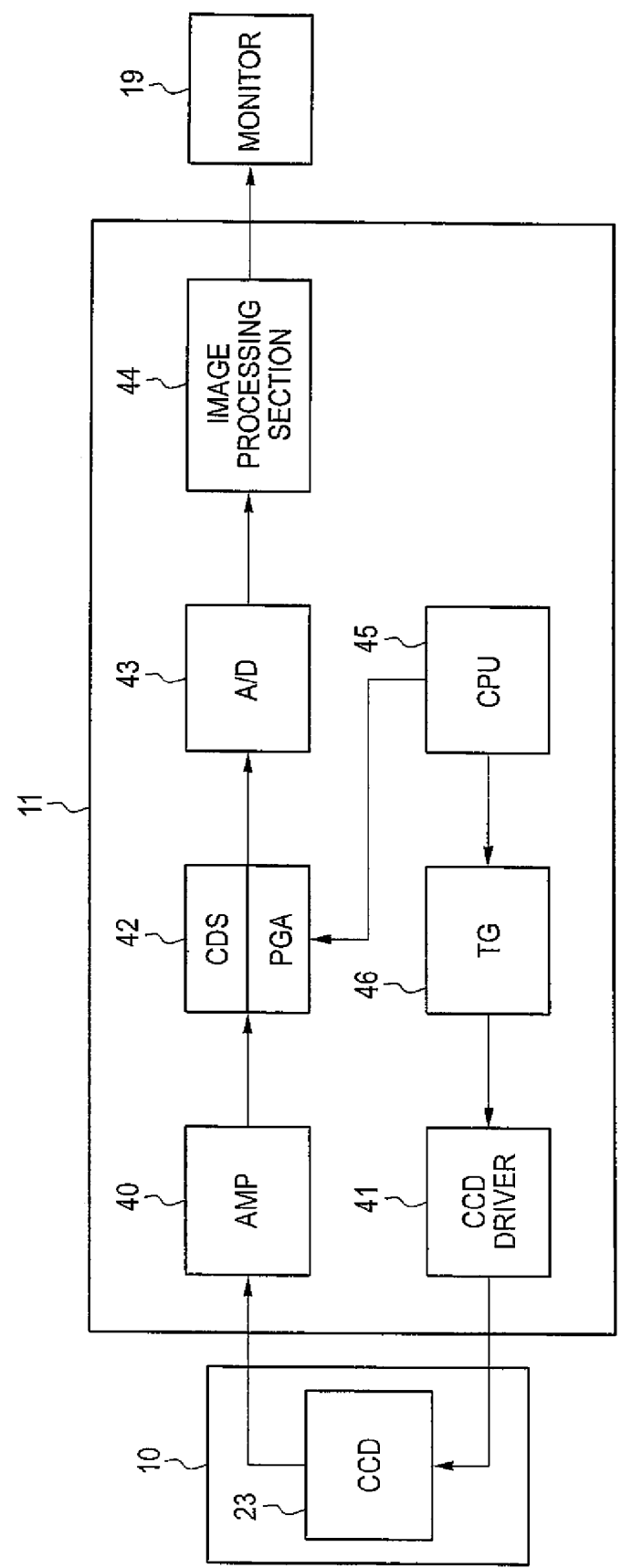
FIG. 4 is a block diagram showing an electric constitution of the electronic endoscope system.

In FIG. 4, CCD 23 is connected with an amplifier (hereinafter, abbreviated as AMP) 40 and a CCD driver 41 provided to the processor apparatus 11. AMP 40 amplifies the imaging signal output from CCD 23 by a gain to output to a correlation double sampling programmable gain amplifier (hereinafter, abbreviated as CDS/PGA) 42.

CDS/PGA 42 outputs the imaging signal outputted from AMP 40 as image data of R, G, B accurately in correspondence with stored electric charge amounts of respective cells of CCD 23 and amplifies the image data to output to an A/D converter (hereinafter, abbreviated as A/D) 43. A/D 43 converts analog image data outputted from CDS/PGA 42 into digital image data. An image processing section 44 subjects image data digitized by A/D 43 to various image processings to output the image inside of the coelom to the monitor 19.

The CCD driver 41 is connected with a timing generator (hereinafter, abbreviated as TG) 46 controlled by CPU 45. The CCD driver 41 controls a shutter speed of an electronic shutter of CCD 23 by a timing signal (clock pulse) inputted from TG 46.

When the inside of the coelom is observed by the electronic endoscope system 2 constituted as described above, the light source apparatus is made ON, the inserting portion 12 is inserted into the coelom, and the image inside of the coelom by CCD 23 is observed by the monitor 19 while illuminating the inside of the coelom.

When the power source of the electronic endoscope 10 is made ON, the CCD driver 41 and the like are started and the image light of the observed portion is taken by CCD 23. The image light of the observed portion taken in from the object optical system 21 or the like is focused onto the imaging surface 23a by way of the prism 24, thereby, the imaging signal is output from CCD 23.

The imaging signal outputted from CCD 23 is amplified by AMP 40, subjected to correlation double sampling and amplification by CDS/PGA 42, and converted into the digital image data by A/D 43. The image data digitized by A/D 43 is subjected to various image processings by the image processing section 44, thereafter, displayed on the monitor 19 as the image.

When CCD 23 is driven, the peripheral circuit 27 generates heat, and the first circuit board 28 mounted with the peripheral circuit 27 is heated. The thermal conductivity of the first circuit board 28 is lower than that of the circuit board whose major component is alumina, and therefore, in comparison with the case of using the circuit board whose major component is alumina, heat from the peripheral circuit 27 is more stored. That is, the heat of the peripheral circuit 27 is difficult to be transferred to the cable 30 and the heat is difficult to escape to the side of the operating portion 13. The first circuit board 28 is arranged at the vicinity of the upper surface of the cover glass 26, and therefore, the heat of the first circuit board 28 reaches to warm up an outer face of the cover glass 26 (a face on a side of being connected with the prism 24).

Here, whereas the outer surface of the cover glass is cooled when the power source of the electronic endoscope 10 is made ON, or when cleaning water or air is injected to the observation window 20, an inner surface of the cover glass (a surface on a side of CCD 23) is heated by heat of driving CCD 23 and the second circuit board 32. Therefore, a temperature difference is produced between the outer surface and the inner surface of the cover glass 26 and dew condensation is brought about at the inner face of the cover glass 26. However, the outer surface of the cover glass 26 is warmed up by the heat of the first circuit board 28 having the thermal conductivity lower than that of the circuit board whose major component is alumina, and therefore, the outer surface and the inner surface of the cover glass 26 is brought into a thermally balanced state to prevent dew condensation.

As explained above, the thermal conductivity of the first circuit board 28 arranged at the vicinity of the upper surface of the cover glass 26 is made to be lower than that of the circuit board whose major component is alumina, and therefore, dew condensation of the cover glass 26 can firmly be prevented without providing a board having a special shape or a heater.

Further, it is not necessary to provide an extraneous member of a board having a special shape or a heater, and therefore, space conservation can be realized, which can contribute to slender diameter formation of the front end portion 12a, and therefore, inserting portion 12. Further, only the material of the first circuit board 28 is changed, and therefore, the invention is applicable to an existing electronic endoscope without considerably changing the specification.

Further, in addition to using the first circuit board 28 having the thermal conductivity lower than that of the circuit board whose major component is alumina, there may be used the second circuit board 32 having the thermal conductivity higher than that of the circuit constitution whose major component is alumina. Specifically, there is used the second circuit board 32 having the thermal conductivity at least 5 times as much as that of the circuit board whose major component is alumina or more, or 5 times through 10 times or more of the thermal conductivity of the circuit board whose major component is alumina as a preferable range. As a material satisfying the above-described condition, for example, there is pointed out an aluminum nitride board (thermal conductivity 80 through 150 W/mK) formed by baking a material whose major component is aluminum nitride at a high temperature.

When the above-described second circuit board 32 is used in addition to the first circuit board 28, in comparison with the case of using the circuit board whose major component is alumina, heat of driving CCD 23 and the second circuit board 32 per se is radiated efficiently to outside by transferring through the signal line 34. Therefore, as a result, the temperature difference between the outer surface and the inner surface of the cover glass 26 is reduced. Therefore, in comparison with the case of using only the first circuit board 28 having the thermal conductivity lower than that of the circuit board whose major component is alumina, dew condensation of the cover glass 26 can further firmly be prevented.

Although according to the above-described embodiment, the spacer 25 is used such that CCD 23 and the cover glass 26 are spaced apart from each other by the gap therebetween, in place of the spacer 25, a transparent adhering agent may be used, or the cover glass 26 may be formed with a leg. Further, although circuits of AMP 40, the CCD driver 41 and the like are mounted to a side of the processor apparatus 11, the circuits may be provided on a side of the electronic endoscope 10.

Further, although according to the embodiment, an explanation has been given by taking the example of the electronic endoscope 10 of so-to-speak a straight viewing type in which the optical axis 21*a* of the object optical system 21 is attached in parallel with the center axis 12*b* of the inserting portion 12, the invention is applicable also to an electronic endoscope of a side viewing type in which the center axis 12*b* and the optical axis 21*a* are orthogonal to each other.

This application claims foreign priority from Japanese Patent Application No. 2007-87026, filed Mar. 29, 2007, the entire disclosure of which is herein incorporated by reference.

What is claimed is:

1. An imaging apparatus comprising:
    a solid-state imaging device that receives image light of an observed portion inside of a coelom to output an imaging signal of the image light;
    a cover glass disposed above a light receiving surface of the solid-state imaging device so that the cover glass and the solid-state imaging device are separated with a space;
    a first circuit board disposed at a distance from the cover glass and including a peripheral circuit of the solid-state imaging device, the first circuit board having a thermal conductivity lower than 10 W/mK, wherein a major component of the first circuit board is a mixture material of alumina and glass; and
    a second circuit board disposed at a lower surface or a side surface of the solid-state imaging device and including a second peripheral circuit of the solid-state imaging device, the second circuit board having a thermal conductivity higher than that of the reference circuit board,
    the imaging apparatus being included in a front end of an electronic endoscope and the imaging apparatus further comprising a sealing agent sealing the peripheral circuit and the sealing agent contacting the cover glass and the first circuit board, wherein
    an amount of the alumina in the mixture material is 40 to 60% and an amount of the glass in the mixture material is 40 to 60%.

2. The imaging apparatus according to claim 1, wherein the thermal conductivity of the first circuit board is at least equal to or lower than ⅕ of that of the reference circuit board.

3. The imaging apparatus according to claim 1, wherein the thermal conductivity of the second circuit board is at least 5 times as much as that of the reference circuit board.

4. An electronic endoscope comprising an imaging apparatus according to claim 1 at a front end thereof.

* * * * *